United States Patent [19]
LaBella et al.

[11] Patent Number: 5,451,200
[45] Date of Patent: Sep. 19, 1995

[54] BODY BRACE

[75] Inventors: Salvatore F. LaBella, Springfield; James F. J. Tierney, West Yarmouth, both of Mass.

[73] Assignee: Spinal Technology, Inc., West Yarmouth, Mass.

[21] Appl. No.: 243,788

[22] Filed: May 17, 1994

[51] Int. Cl.[6] .............................................. A61F 5/00
[52] U.S. Cl. .......................................... 602/19; 2/45
[58] Field of Search ................. 602/18, 19; 2/44, 45

[56] References Cited

U.S. PATENT DOCUMENTS

| | | |
|---|---|---|
| 2,655,916 | 10/1953 | Timmins . |
| 3,717,143 | 2/1973 | Johnson . |
| 3,871,367 | 3/1975 | Miller . |
| 4,022,197 | 5/1977 | Castiglia . |
| 4,076,022 | 2/1978 | Walker . |
| 4,178,923 | 12/1979 | Curlee . |
| 4,202,327 | 5/1980 | Glancy . |
| 4,383,523 | 5/1983 | Schurman ............................ 602/18 |
| 4,559,933 | 12/1985 | Batard et al. . |
| 4,628,913 | 12/1986 | Lerman ................................ 602/18 |
| 4,688,558 | 8/1987 | Hooper, Jr. . |
| 4,712,540 | 12/1987 | Tucker et al. ...................... 602/18 |
| 5,072,725 | 12/1991 | Miller . |
| 5,074,288 | 12/1991 | Miller . |
| 5,158,531 | 10/1992 | Zamosky . |
| 5,256,135 | 10/1993 | Avihod . |
| 5,259,831 | 11/1993 | Lebron . |
| 5,267,948 | 12/1993 | Elliott ................................. 602/19 |

*Primary Examiner*—Linda C. M. Dvorak
*Attorney, Agent, or Firm*—Ross, Ross & Flavin

[57] ABSTRACT

A body brace or orthotic device to be worn on the torso of a patient for the correction of spinal abnormalities and comprising a hard outer shell and a soft inner liner semi-permanently attached thereto and adapted for easy removal for cleaning, repair, or replacement, and permitting cutting away of openings at strategic locations wherein pressure on the torso of the patient is not desired, while retaining the soft integrity Of the liner to achieve desired control of pressure sensitive areas.

1 Claim, 6 Drawing Sheets

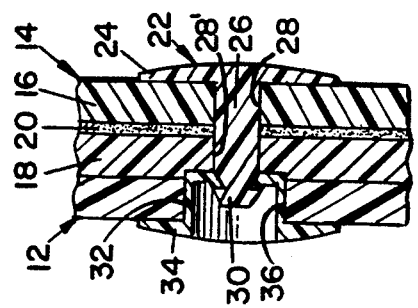
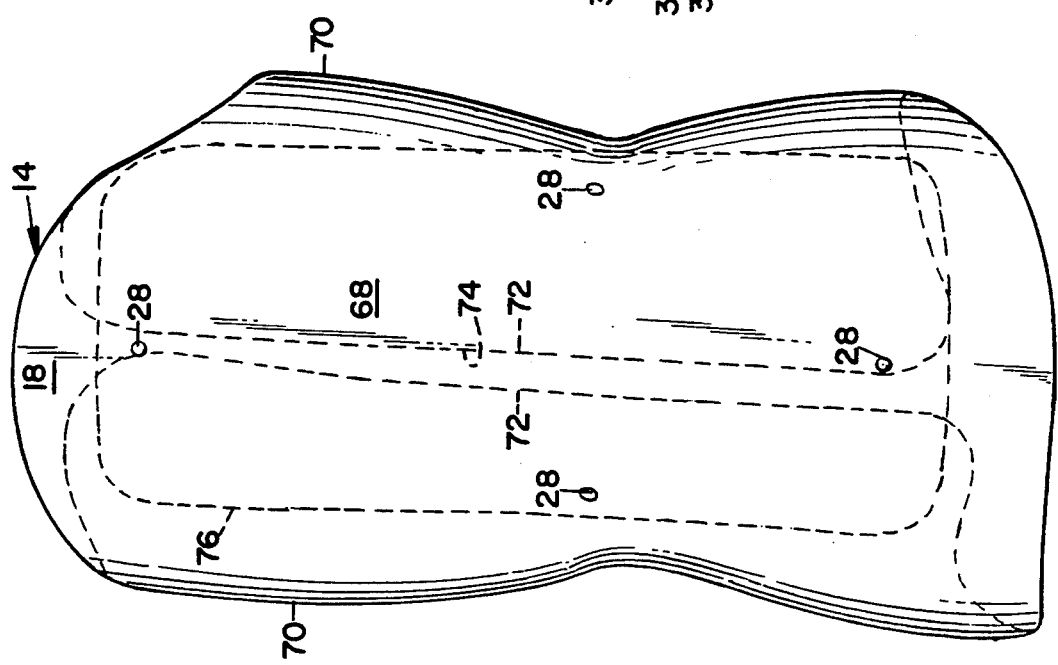
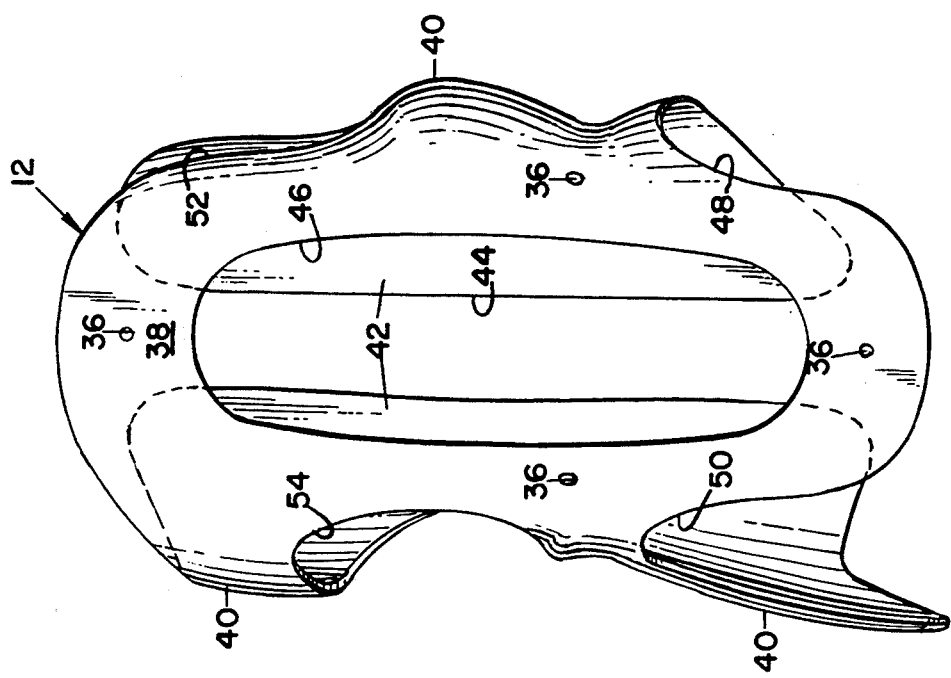

BODY BRACE

BACKGROUND OF THE INVENTION

1. Field of the Invention

The invention relates to body braces to be worn by a patient for the orthotic treatment of disorders of the spinal column such as scoliosis, kyphosis, or other spinal abnormalities.

2. Description of the Prior Art

A wide variety of orthoses or body braces which conform to the torso of a patient is available to be worn for the treatment of abnormal curvatures of the spine or other spinal abnormalities.

Some include a hard outer shell having a soft inner liner which presses directly against the body of the patient.

However, the soft inner liner is permanently attached to the shell as by heat sealing or by an adhesive to form an inseparable unit.

Thus, if the inner liner becomes soiled or damaged it cannot be removed for repair, cleaning or replacement. Therefore, the entire orthotic device must be discarded.

Also, if the inner liner cannot be separated from the outer shell, it is extremely difficult to cut away the outer shell to provide openings at strategic locations while retaining the soft integrity of the inner liner to achieve the desired results.

Herein, thermo plastic fasteners affix the liner to the shell, the fasteners being easily cut to separate the liner from the shell.

SUMMARY OF THE INVENTION

The invention hereof provides a body brace or orthotic device to be applied to the torso of a patient for the correction of spinal abnormalities and comprising a hard outer shell and a soft inner liner semi-permanently attached thereto. The inner liner may be easily separated from the shell for cleaning, repair, or replacement.

Portions of the shell may also be cut away to provide openings at strategic locations wherein pressure on the torso of the patient is not desired, while retaining the soft integrity of the liner to achieve the desired control of pressure sensitive areas.

BRIEF DESCRIPTION OF THE DRAWINGS

FIG. 7 is a rear elevational view of the outer shell of FIG. 5 with parts omitted;

FIG. 8 is a rear elevational view of the inner liner of FIG. 6 with parts omitted; and FIG. 9 is an enlarged, fragmentary, cross-sectional view taken on line 9—9 of FIG. 3.

DESCRIPTION OF THE PREFERRED EMBODIMENT

Figure 1:
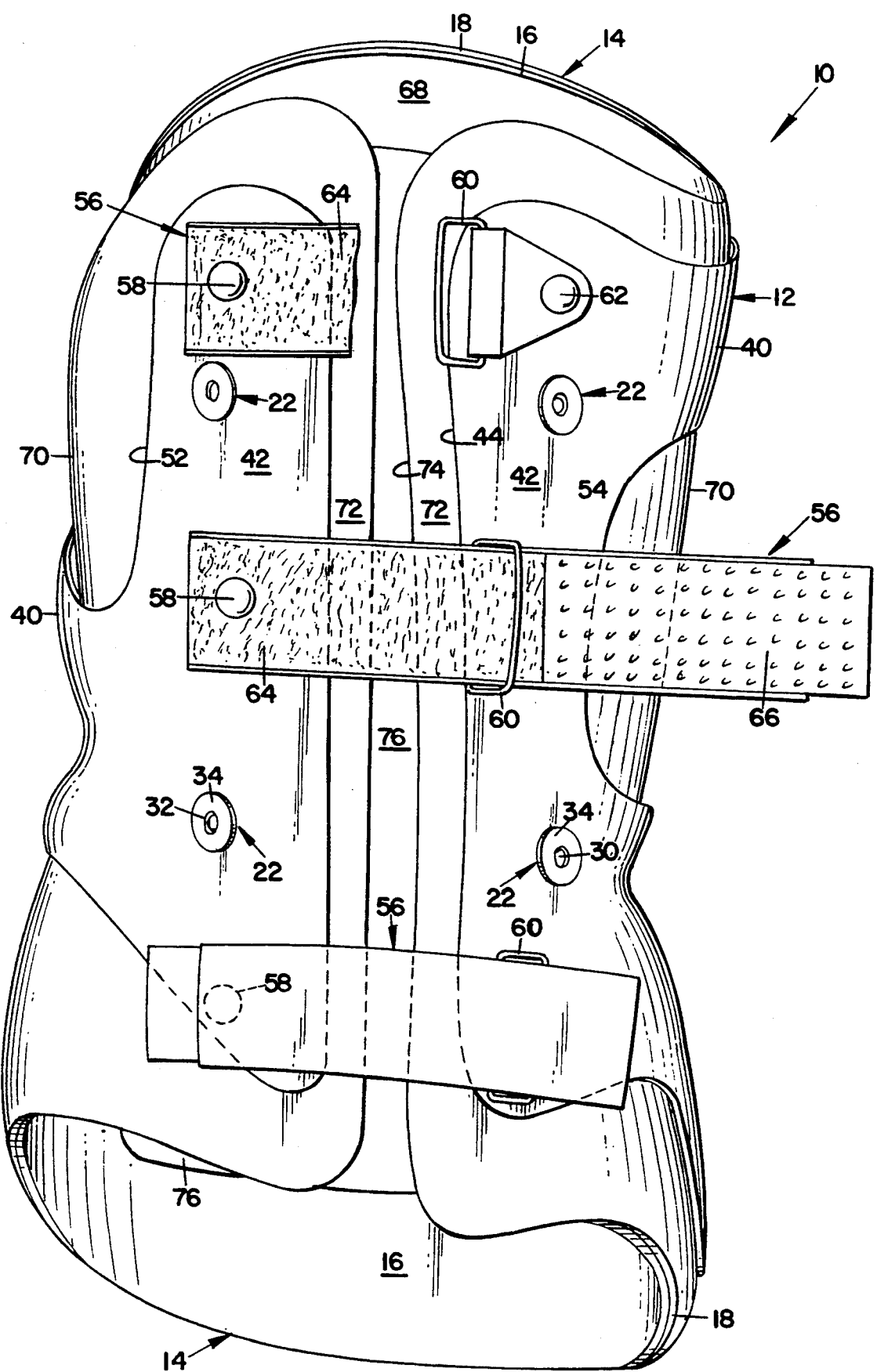
FIG. 1 is a front elevational view of a body brace embodying the invention.
Figure 2:
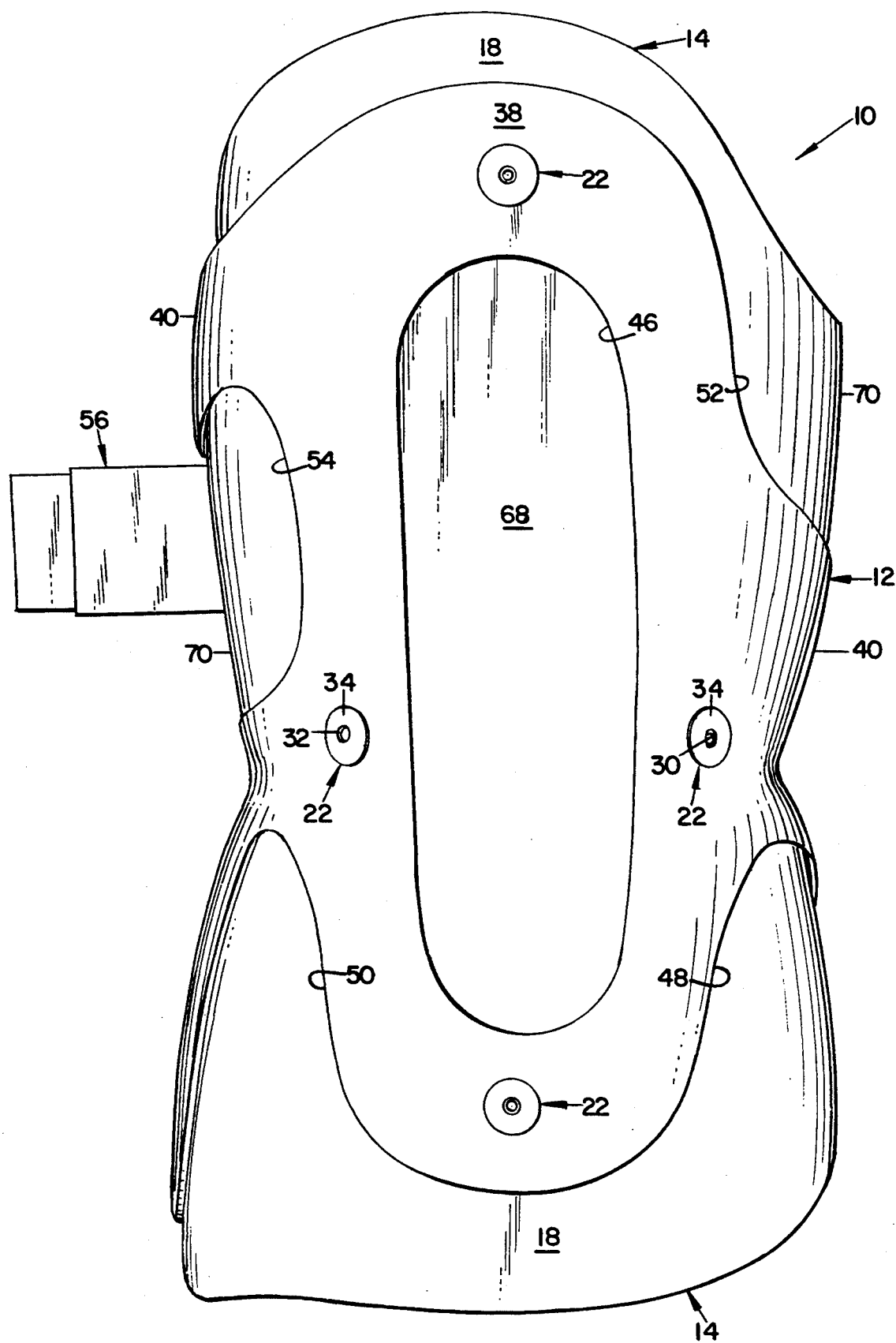
FIG. 2 is a rear elevational view.
Figure 3:
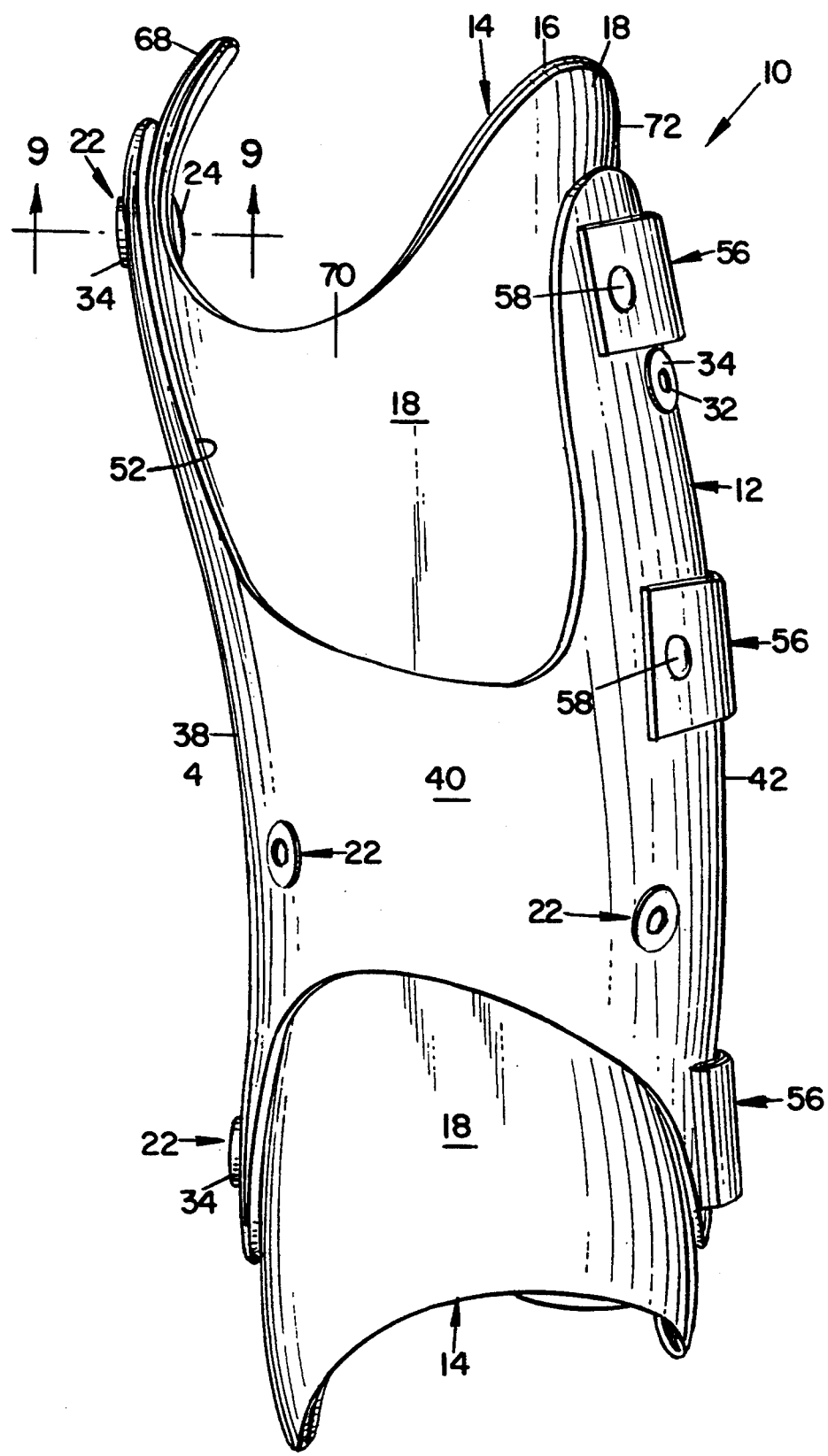
FIG. 3 is a side elevational view as seen from the left of FIG. 1.
Figure 4:
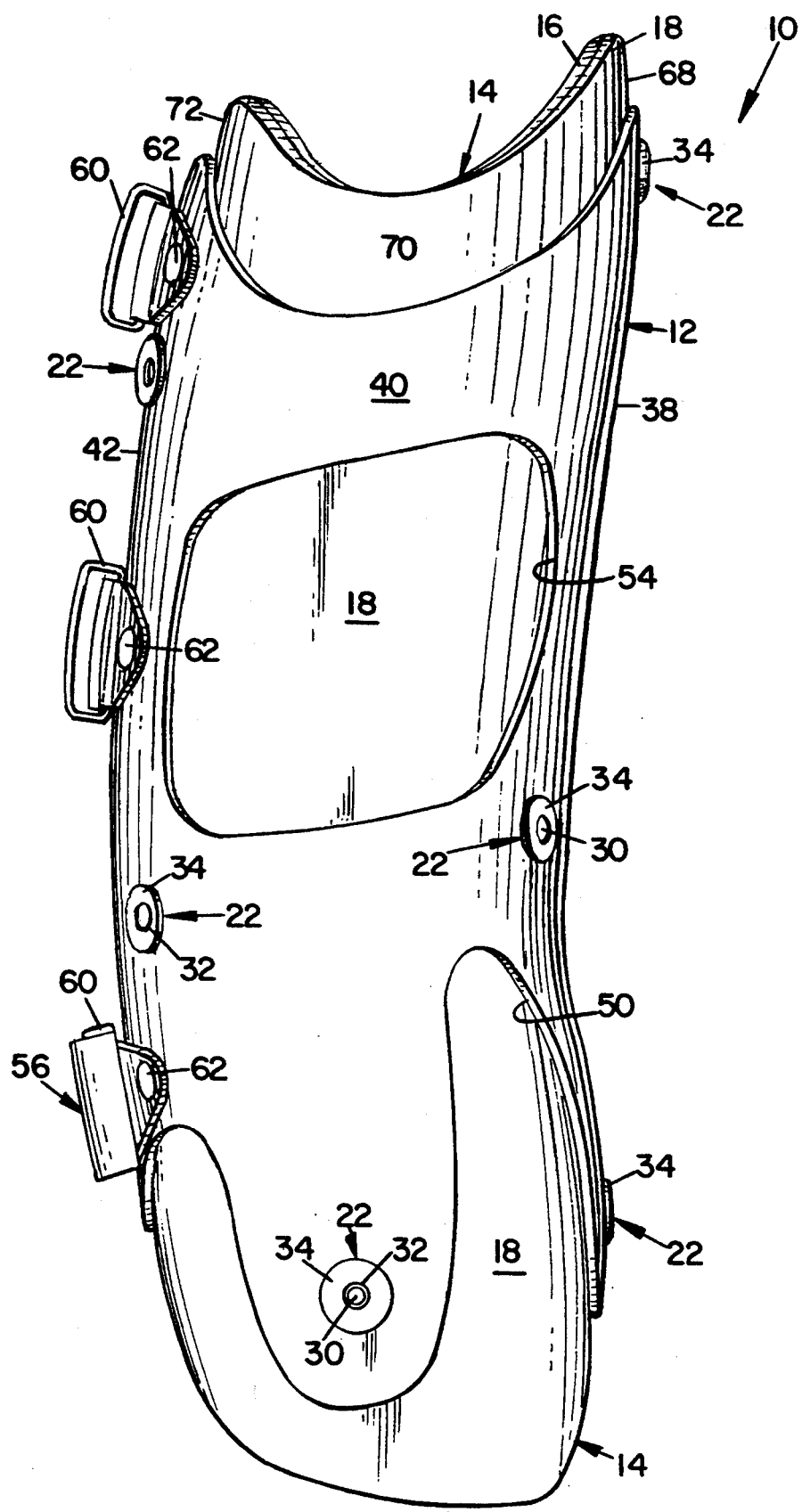
FIG. 4 is a side elevational view as seen from the right of FIG. 1.
Figure 6:
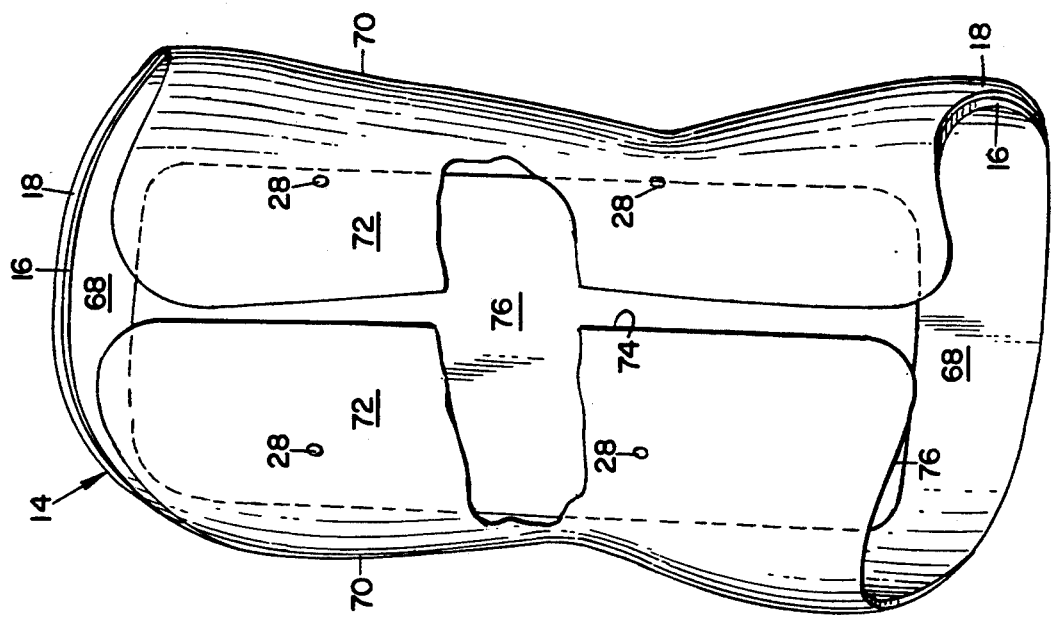
FIG. 6 is a front elevational view of the inner liner of the body brace, with parts omitted and other parts broken away.
Figure 5:
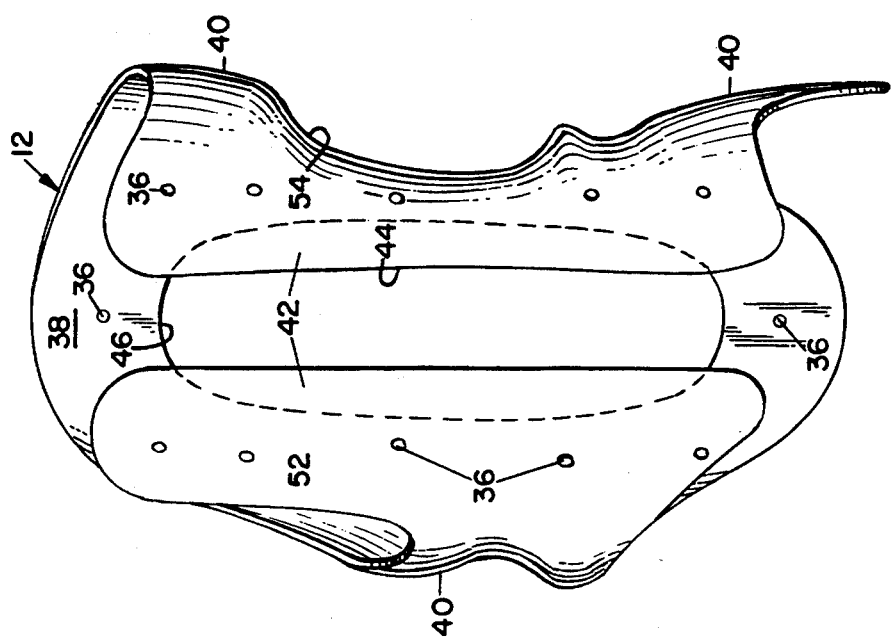
FIG. 5 is a front elevational view of the outer shell of the body brace, with parts omitted.

Referring to the drawings, a body brace 10 embodying a preferred form of the invention is of appropriate configuration to embrace a selected portion of a human torso, not shown, and includes a rigid vest-like outer shell 12 fabricated from a hard, low density copolymer thermoplastic such as a mix of polyethylene and buterate, or a mix of polyproplylene and polyethylene.

The particular body brace shown in the drawings is of the so-called "high profile" type and extends between the chest and hips of the patient for controlling or maintaining scoliotic curvature, and other spinal abnormalities with the outer shell matching the spinal curvature of the patient.

Alternatively, the body brace can be of a "low profile" type and be worn over a smaller portion of the body to treat other muscular skeletal problems.

Outer shell 12 encases an inner liner 14 which is preferably of two ply construction and comprises a soft polyethylene low density inner ply 16 which contacts the body of the patient and a harder more durable high density polyethylene foam outer ply 18 disposed adjacent the inner surface of outer shell 12.

As best seen in FIG. 9, a suitable adhesive 20 is sandwiched between inner ply 16 and outer ply 18 to bond the plies together.

Again referring to FIG. 9, inner liner 14 is fixed to outer shell 12 by a plurality of fasteners comprising locking rivets 22 which include a head 24 bearing against the inner liner and a shank 26 which extends through provided openings 28 and 28' in the plies of the inner liner and has an inner locking tip 30 lockably receivable in a central opening 32 of a boss 32' of a grommet-like locking ring 34 resting against the outer face of outer shell 12, with boss 32' extending inwardly through an opening 36 in outer shell 12 and aligned with openings 28 and 28' of inner liner 14.

Locking rivets 22 and locking rings 34 are preferably fabricated from any sturdy thermoplastic material.

The liner and shell may easily be separated from each other by the simple expedient of cutting through shanks 26 of locking rivets 22 with any appropriate cutting tool permitting separation and removal of the liner from the shell.

This is a highly desirable feature greatly facilitating the cleaning, repair or replacement of the inner liner, and enhancing the ability to cut away openings in the outer shell at strategic locations while retaining the soft integrity of the liner when pressure on the torso of the patient is not desired.

The ability to separate the liner from the shell is a great advantage over body braces of the prior art in which the inner liners are heat bonded to the outer shell or bonded with an adhesive to the outer shell, wherefore the liners cannot be separated or removed from the shell for replacement or cleaning if they become soiled or damaged, therefore not providing the ability to cut away openings at strategic locations when pressure on the torso of the patient is not desired.

Outer shell 12 is vest-like and includes a rear panel 38 disposed adjacent the back of the patient, side panels 40, 40 which enwrap the sides of the patient and a pair of front panels 42, 42 disposed adjacent the chest and abdomen of the patient and separated throughout their length by a longitudinally-extending central opening or slot 44.

The shell may also be worn so that panel 38 is disposed adjacent the chest and abdomen of the patient, with panels 42, 42 and central opening or slot 44 being disposed adjacent the back of the patient.

Additionally, a longitudinally-extending central opening or slot, not shown, similar to central opening or slot 44, may be provided in rear panel 38 of the shell, thus providing a shell with both front and rear central openings.

Depending upon the particular patient condition being treated, the shell may be cut away or relieved at appropriate locations as at a longitudinally-extending central opening 46 and lower cut-outs at 48 and 50 in rear panel 38 and similar upper cut-out 52 and 54 which are disposed between side panels 40, 40 and front panels 42, 42.

The size, location and number of cut outs may vary depending upon the spinal condition of the patient to be corrected by the body brace.

Or, the shell may be solid throughout with no cut-outs.

The body brace may be tightly secured to the torso of the patient as by a plurality of spaced straps 56 which extend transversely between front panels 42, 42 of outer shell 12 across central opening or slot 44.

If a central opening is provided in rear panel 38 as indicated above, spaced straps, not shown, similar to straps 56, may be employed to span such opening and further secure the body brace to the torso of the patient.

Straps 56 are fixed at one end as by rivets 58 to one front panel 42 and have a free outer end which passes through a buckle 60 fixed to the other front panel 42 as by a rivet 62 and are folded back upon themselves to bring VELCRO patches 64 and 66 fixed to the inner face of each strap into engagement with each other.

This strap arrangement provides for quick and easy donning and removal of the body brace.

As aforesaid, shell 12 encases liner 14.

Liner 14 includes a rear panel 68 disposed inwardly of shell rear panel 38 and adapted to bear against the back of the patient, side panels 70, 70 disposed inwardly of shell side panels 40, 40 and enwrapping the sides of the patient, and a pair of front panels 72, 72 disposed inwardly of shell front panels 42, 42 and adapted to bear against the chest and abdomen of the patient. Front panels 72, 72 are separated throughout their length by a longitudinally-extending central opening or slot 74.

A rectangular flap 76 is fixed along one side edge to a rear face of one front panel 72. The other side edge of the flap is unattached and is disposed rearwardly of the other front panel. The flap is of sufficient width as to bridge central opening 74 between the liner front panels.

Flap 76 ensures against any rubbing of straps 56 against the body of the patient, thereby contributing to wearer comfort.

If a central opening is provided in the rear panel of shell 12, a similar central opening, not shown, will be provided in rear panel 68 of liner 14, and that opening will be bridged by a flap, not shown, similar to flap 76.

We claim:

1. An orthotic device in the form of a body brace to be worn on the torso of a patient for the correction of spinal abnormalities comprising:

a hard outer shell fabricated from a hard, low density copolymer thermoplastic, an inner liner encased by the shell, the inner liner being of laminated two ply construction and comprising a soft polyethylene low density inner ply adapted to contact the body of the patient and a harder more durable high density polyethylene foam outer ply fixed to the inner ply and disposed adjacent the inner surface of the hard outer shell, the outer shell and inner liner configured to conform to the torso of the patient with areas of the outer shell only being cut away to provide openings at strategic locations to achieve the desired control or correction of pressure sensitive areas, while the inner liner continues to provide patient support in those areas, and means for semi-permanently attaching the liner to the shell comprising thermoplastic locking rivets which extend through the shell and the liner and are receivable in thermoplastic locking rings on the shell for permitting easy separation of the liner from the shell for cleaning, repair or replacement and permitting cutting away of the outer shell to provide openings at strategic locations while retaining the integrity of the inner liner to achieve the desired support.

* * * * *